(12) United States Patent
Dang et al.

(10) Patent No.: US 7,118,592 B1
(45) Date of Patent: Oct. 10, 2006

(54) COVERED STENT ASSEMBLY FOR REDUCED-SHORTENING DURING STENT EXPANSION

(75) Inventors: Kenny L. Dang, San Jose, CA (US); Han Juanta, Milpitas, CA (US); Nazanine Matin, Palo Alto, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 1164 days.

(21) Appl. No.: 09/660,812

(22) Filed: Sep. 12, 2000

(51) Int. Cl.
*A61F 2/06* (2006.01)

(52) U.S. Cl. ............... 623/1.12; 623/1.46; 606/194; 606/198

(58) Field of Classification Search ............ 623/23.7, 623/1.15, 1.44–1.48, 1.12, 1.42; 606/191, 606/192, 194, 195, 198; 427/2.25
See application file for complete search history.

(56) References Cited

U.S. PATENT DOCUMENTS

| | | | |
|---|---|---|---|
| 4,776,337 A | | 10/1988 | Palmaz |
| 5,445,646 A | * | 8/1995 | Euteneuer et al. .......... 606/198 |
| 5,824,046 A | | 10/1998 | Smith et al. |
| 6,099,559 A | | 8/2000 | Nolting |
| 6,099,561 A | | 8/2000 | Alt |
| 6,120,536 A | | 9/2000 | Ding et al. |
| 6,139,573 A | | 10/2000 | Sogard et al. |
| 6,143,022 A | | 11/2000 | Shull et al. |
| 4,776,337 A | | 12/2000 | Palmaz |
| 6,156,064 A | | 12/2000 | Chouinard |
| 6,159,239 A | | 12/2000 | Greenhalgh |
| 6,162,244 A | | 12/2000 | Braun et al. |
| 6,165,211 A | | 12/2000 | Thompson |
| 6,168,619 B1 | | 1/2001 | Dinh et al. |
| 6,254,627 B1 | * | 7/2001 | Freidberg ............... 606/195 |
| 6,315,794 B1 | | 11/2001 | Richter |
| 2001/0021870 A1 | | 9/2001 | Edwin et al. |
| 2001/0032009 A1 | | 10/2001 | Layne et al. |
| 2001/0039446 A1 | | 11/2001 | Edwin et al. |

FOREIGN PATENT DOCUMENTS

| | | |
|---|---|---|
| WO | WO 96/00103 | 1/1996 |
| WO | WO 99/15105 | 4/1999 |

OTHER PUBLICATIONS

U.S. application Ser. No. 09/610,577 filed Jul. 5, 2000.

\* cited by examiner

*Primary Examiner*—David J. Isabella
*Assistant Examiner*—Urmi Chattopadhyay
(74) *Attorney, Agent, or Firm*—Fulwider Patton Lee & Utecht, LLP

(57) ABSTRACT

A polymeric material such as polyurethane, PET, or ePTFE is used to cover an intravascular stent. The cover material has an overlapping portion which is slidable upon itself so that when the stent is expanded, the cover material does not contribute to stent foreshortening, if any. The cover material can be provided with holes to permit endothelialization and can be drug loaded to facilitate repair of a damaged vessel.

22 Claims, 3 Drawing Sheets

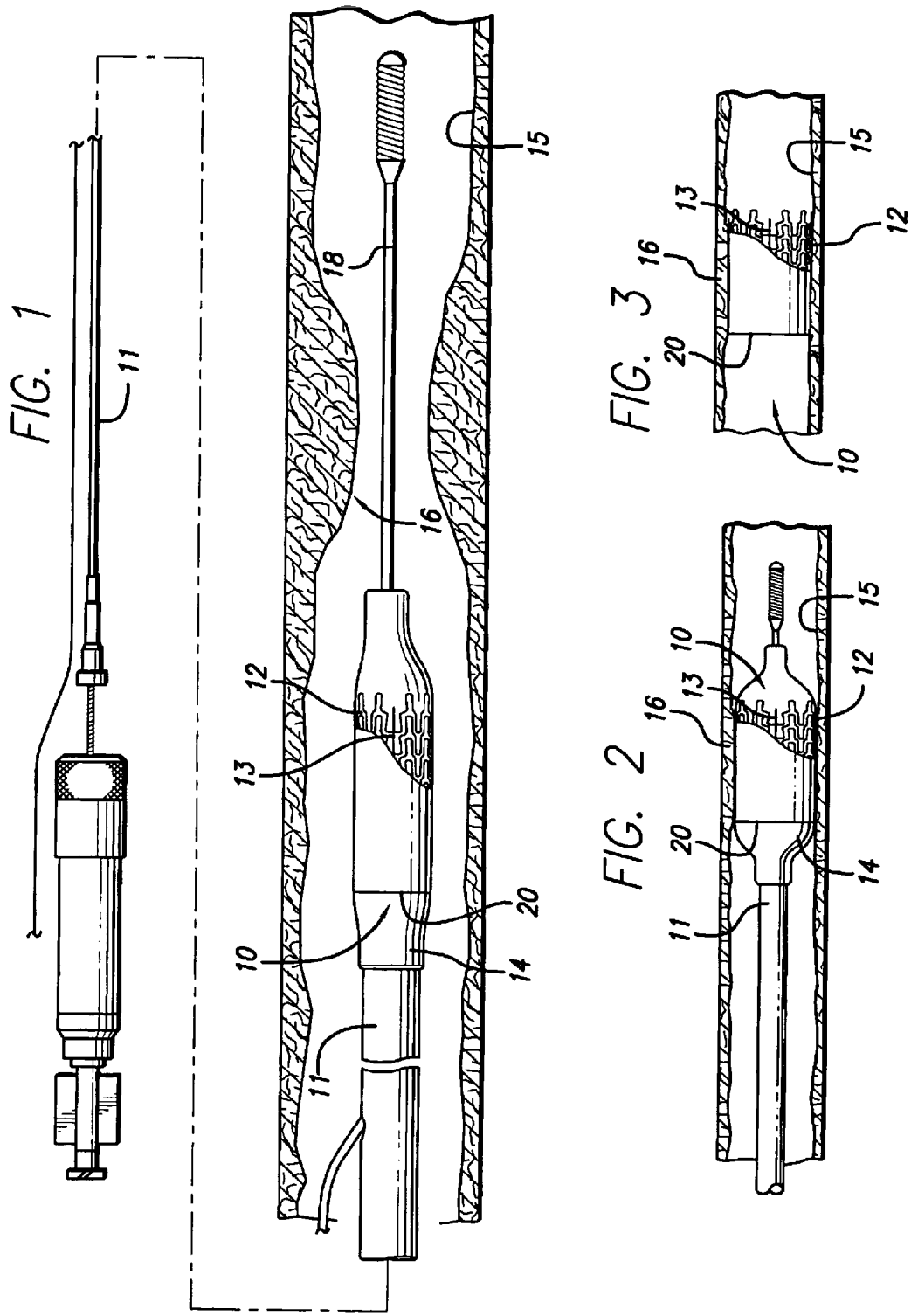

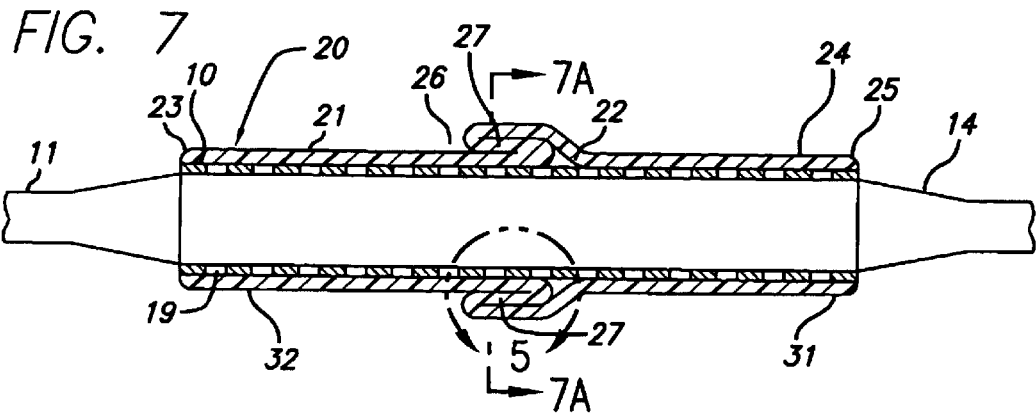
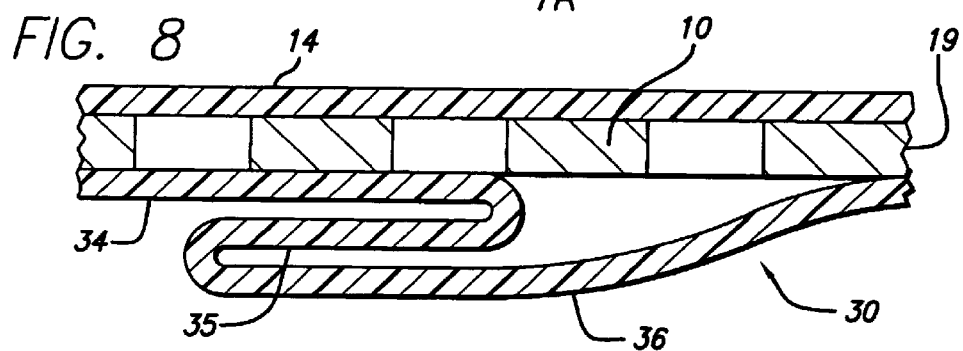
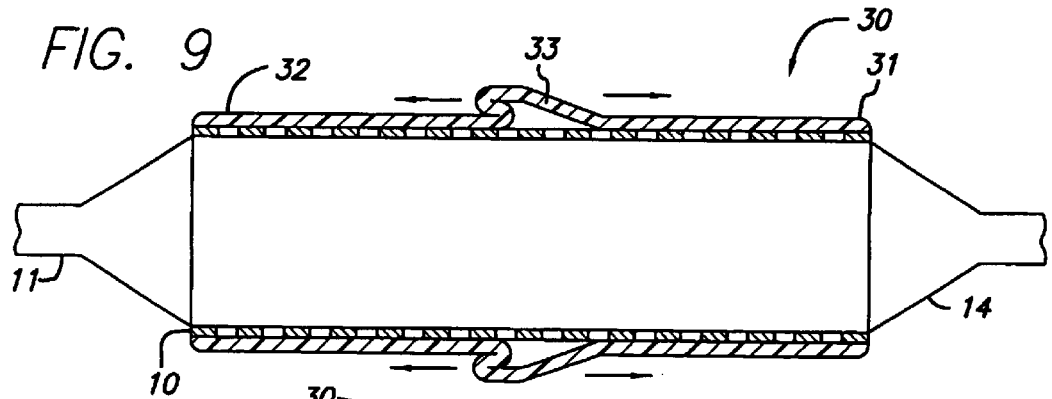
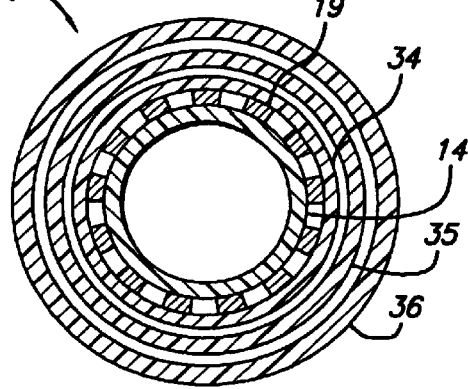

COVERED STENT ASSEMBLY FOR REDUCED-SHORTENING DURING STENT EXPANSION

BACKGROUND OF THE INVENTION

The present invention relates generally to expandable endoprosthesis devices, generally called stents, which are adapted to be implanted into a patient's body lumen, such as a blood vessel, to maintain the patency thereof, and more particularly to covered vascular stents which can minimize plaque prolapse that can occur between the struts of the stent and can help prevent the formation and release of embolic debris into the body lumen. Stents are particularly useful in the treatment and repair of blood vessels after a stenosis has been compressed by percutaneous transluminal coronary angioplasty (PTCA), percutaneous transluminal angioplasty (PTA), or removed by atherectomy or other means, to help improve the results of the procedure and reduce the possibility of restenosis. Stents also can be used to provide primary compression to a stenosis in cases in which no initial PTCA or PTA procedure is performed. While stents are most often used in the procedures mentioned above, they also can be implanted in any body lumen or vessel such as the urethra, esophagus and bile duct and the like.

In typical PTCA procedures, a guiding catheter or sheath is percutaneously introduced into the cardiovascular system of a patient through the femoral arteries and advanced through the vasculature until the distal end of the guiding catheter is in the aorta. A guide wire and a dilatation catheter having a balloon on the distal end are introduced through the guiding catheter with the guide wire sliding within the dilatation catheter. The guide wire is first advanced out of the guiding catheter into the patient's vasculature and is directed across the arterial lesion. The dilatation catheter is subsequently advanced over the previously advanced guide wire until the dilatation balloon is properly positioned across the arterial lesion. Once in position across the lesion, the expandable balloon is inflated to a predetermined size with a radiopaque liquid at relatively high pressure to displace the atherosclerotic plaque of the lesion against the inside of the artery wall and thereby dilate the lumen of the artery. The balloon is then deflated to a small profile so that the dilatation catheter can be withdrawn from the patient's vasculature and the blood flow resumed through the dilated artery. As should be appreciated by those skilled in the art, while the above-described procedure is typical, it is not the only method used in angioplasty.

In angioplasty procedures of the kind referenced above, abrupt reclosure may occur or restenosis of the artery may develop over time, which may require another angioplasty procedure, a surgical bypass operation, or some other method of repairing or strengthening the area. To reduce the likelihood of the occurrence of abrupt reclosure and to strengthen the area, a physician can implant an intravascular prosthesis for maintaining vascular patency, commonly known as a stent, inside the artery across the lesion. Stents are generally cylindrically shaped devices which function to hold open and sometimes expand a segment of a blood vessel or other arterial lumen, such as coronary artery. Stents are usually delivered in a compressed condition to the target location and then are deployed into an expanded condition to support the vessel and help maintain it in an open position. The stent is usually crimped tightly onto a delivery catheter and transported in its delivery diameter through the patient's vasculature. The stent is expandable upon application of a controlled force, often through the inflation of the balloon portion of the delivery catheter, which expands the compressed stent to a larger diameter to be left in place within the artery at the target location. The stent also may be of the self-expanding type formed from, for example, shape memory metals or super-elastic nickel-titanium (NiTi) alloys, which will automatically expand from a compressed state when the stent is advanced out of the distal end of the delivery catheter into the body lumen.

Details of prior art expandable stents can be found in U.S. Pat. No. 3,868,956 (Alfidi et al.); U.S. Pat. No. 4,512,338 (Balko et al.); U.S. Pat. No. 4,553,545 (Maass, et al.); U.S. Pat. No. 4,733,665 (Palmaz);. U.S. Pat. No. 4,762,128 (Rosenbluth); U.S. Pat. No. 4,800,882 (Gianturco); U.S. Pat. No. 5,514,154 (Lau, et al.); U.S. Pat. No. 5,421,955 (Lau et al.); U.S. Pat. No. 5,603,721 (Lau et al.); U.S. Pat. No. 4,655,772 (Wallsten); U.S. Pat. No. 4,739,762 (Palmaz); and U.S. Pat. No. 5,569,295 (Lam).

Further details of prior art self-expanding stents can be found in U.S. Pat. No. 4,580,568 (Gianturco); and U.S. Pat. No. 4,830,003 (Wolff, et al.).

The above-described, non-surgical interventional procedures, when successful, avoid the necessity for major surgical operations. However, a danger which is always present during these procedures is the potential for particles of the atherosclerotic plaque, which can be extremely friable, breaking away from the arterial wall. For example, during deployment of a stent, the metal struts of the stent can possibly cut into the stenosis and shear off pieces of plaque which become embolic debris that will travel downstream and lodge somewhere in the patient's vascular system. When any of the above-described procedures are performed in the carotid arteries, the release of emboli into the circulatory system should be avoided. Debris that is carried by the bloodstream to distal vessels of the brain can cause these cerebral vessels to occlude, possibly resulting in a stroke. Therefore, although cerebral percutaneous transluminal angioplasty has been performed in the past, the number of procedures performed has been limited due to the fear of causing an embolic stroke should embolic debris enter the bloodstream and block vital downstream blood passages. Embolization in other vasculature may induce possible acute myocardial infraction when a procedure is performed on the coronary arteries and gangrene when performed in peripheral arteries, such as the arms and legs.

While stents are helpful in holding open otherwise blocked or occluded vessels, the stent does have an open structure of struts and spines which cooperatively provide the scaffolding necessary to maintain the vessel open at the site of treatment. Due to the open nature of the stent structure, there is a possibility that growth material can pass through the openings between the struts and extend into the inner lumen of the stent structure. For example, excessive cell or tissue growth (intimal hyperplasia) can cause partial restenosis to develop over time, which is detrimental to the patient. The tissue or cell growth can extend into the tubular opening created by the stent and can block or otherwise re-occlude the opening and can possibly cause abnormal blood flow through the stent which can cause formation of thrombi that are detrimental to the patient's health.

Prior art devices have been created to help reduce the passage of such growth through the wall of the deployed stent, including a stent covering which surrounds the open stent. In this manner, the gaps between the stent struts can be covered to prevent material, such as plaque, from prolapsing between the struts. Coverings have included a variety of materials such as ePTFE, autologous vein grafts, pericardium and fibrin. The covering should be sufficiently flexible and expandable to allow the stent to deploy from its collapsed or compressed position to a fully expanded position.

Covered stents also help prevent the struts from cutting into the plaque of the stenosis which helps reduce the possibility of forming embolic debris that can be released into the blood stream, as described above. Moreover, in the event that any embolic debris may be created from the expansion of the stent, the covering could trap the embolic particles against the arterial wall, thus preventing the particles from being released into the bloodstream.

Some prior art covered stents are difficult to manufacture due to the flexibility of the covering and the requirement that the covering be capable of expansion when the stent is deployed within the patient's vasculature. For these reasons, the material used to form the covering may be subjected to intricate processing to obtain the desired flexibility for the covering and to attach the covering to the stent. A covering which does not expand normally can cause the stent to misalign within the body vessel and can cause an nonuniform deployment of the stent. Moreover, some coverings are made from a sheet of material which is rolled into a cylindrical shape by creating a longitudinal seam which runs along the length of the covering and then the covering is attached to the stent. Such coverings can be more susceptible to tearing, especially at the seam, when the stent is expanded.

Some prior art stents that are covered may have a tendency to shorten when expanded and the covered material also shortens, providing an undesirable result. As the stent and the covered material are expanded into contact with an artery or vessel wall, the shortening movement may scrape along the artery wall and cause injury or dislodge plaque material which may embolize. Further, as these prior art covered stents shorten upon expansion, the cover material shortens past the stent struts at the stent ends, leaving a covered stent with exposed stent struts, and not fully covered upon expansion.

Thus, it would be desirable to have a covered vascular stent in which the covering has sufficient expandability and flexibility and can be formed with a thin wall which does not dramatically increase the delivery profile of the device. Such a covered stent should be relatively easy to manufacture as well and it should not affect the stent's ability to be fully deployed within the patient's vasculature. The present invention satisfies these and other needs.

SUMMARY OF THE INVENTION

The present invention is directed to covered stents for implantation in body vessels which will hold up occluded, weakened or damaged portion of the vessels. The present invention provides a covering made from a polymeric material to cover the gaps formed between stent struts in order to minimize embolic events as well as plaque prolapse that can occur between the struts, especially when the device is placed in regions where the plaque is characterized by a friable, grumous-like nature. The present invention provides a composite intraluminal device which includes a tubular shaped stent having distal and proximal ends, along with internal and external surfaces which extend along a longitudinal stent axis. A tubular covering of polymeric material having open distal and proximal ends can be affixed to the underlying stent and can expand with the stent when placed within a body lumen. Because the device is a covered stent and sometimes covered stents shorten more than bare stents, the tubular covering has an overlap portion that shortens when the stent is expanded in order to minimize covered stent shortening.

In one embodiment of the present invention, the stent covering is made from two segments of a tubular material which are affixed to the underlying stent by bonding one end of the one of the segments to the stent, and bonding one end of the second segment to the other end of the stent using bonding materials such as solvents or adhesives. The placement of the bonding material only at the ends of the first and second sections allows the stent sections to fully expand radially without interference from the cover material which will expand with the stent, and which allows the stent to maintain it continuous tubular opening once deployed in the body vessel. The length of each segment is such that they are shorter than the overall length of the stent so that they form an overlapping portion between the distal and proximal ends of the stent. As the stent expands, the overlapping portion of the first segment slides over the overlapping portion of the second segment shortening the overlap portion and thereby minimizing any shrinkage effect that a fully-constrained cover would have on the stent. The tubular coverings preferably are made from seamless tubing of a material which is less susceptible of breaking compared to prior art covered stents. As a result, an intraluminal device made in accordance with the present invention has sufficient structural strength and reduced strain on the stent struts, and is therefore less prone to failure.

In another embodiment of the present invention, the stent covering is made from a single segment of tubular material which is affixed to the underlying stent by bonding the ends of the tubular covering to the stent using bonding materials such as solvents or adhesives. The placement of bonding material only at the ends of the tubular covering allows the covering to fully expand radially without deforming which allows the stent to maintain its continuous tubular opening once deployed in the body vessel. An overlap portion is formed in the cover material between its distal and proximal ends by folding the material to form three layers. As the stent expands, the overlapping layers slide over each other and thus minimize any shrinking effect the cover has on the stent. The tubular covering preferably is made from a seamless tubing of material which is less susceptible of breaking, compared to prior art covered stents which use adhesive to create a seam on the covering. As a result, an intraluminal device made in accordance with the present invention, has sufficient material strength once expanded in the deployed position and results in an expanded stent having circular openings which maintain a normal pattern of blood flow through the area of treatment.

Another embodiment of the present invention utilizes a tubular covering made from polyurethane or polyethylene terephthalate (hereinafter PET), which are also adhesively bonded at the distal and proximal ends of the stent. Polyurethane and PET are also particularly advantageous materials since they possesses excellent flexibility and expandability. Moreover, they also can be easily impregnated with drugs which will be released into the area of treatment to improve the device's performance within the body vessel. The overlap portion can be formed in layers in a single piece of polyurethane or PET or by using two pieces of material as described.

Another aspect of the present invention utilizes an expanded polytetrafluoroethylene (herein after ePTFE) as the material used to create the covering. A covering made from ePTFE can be obtained in an extruded tubing which would be slip fit over the stent in its collapsed or unexpanded position. Again, a bonding material, such as adhesive, can be applied to ends of the stent and/or covering to secure the ePTFE covering to the stent. The ePTFE tubing can have a wall thickness of about 0.0005 to 0.010 inch (approximately 12 to 250 microns). The natural microporosity of ePTFE allows cellular infiltration, thus speeding up the process of endothelialization. Again, the overlap portion can be formed in a single piece or two pieces of ePTFE.

The invention is not intended to be limited so that more than one overlapping portion can be formed in order to minimize covered stent shrinkage. For example, when a single piece of material is used for the covered material, more than one overlapping portion can be formed along its length so that upon stent expansion, the overlapping portions slide relative to each other to minimize stent shortening. Likewise, more than two segments of material can be used to cover the stent and create more than one overlapping portion along the length of the stent.

All of the coverings used in accordance with the present invention can be provided with openings which are formed, for example, by a laser. The material forming the covering also could be formed having a certain degree of porosity. The openings and porous nature of the material allow some cell infiltration through the covering to speed up the process of endothelialization. Such a covering would also allow nutrient transfer to the walls of the vessel from the resulting blood flow. Both of these occurrences would more likely result in better acceptance of the covering by the blood vessel, reducing the chance that the body will reject the implant. The material also can be nonporous, depending upon the particular application to which the covered stent is to be used. Additionally, all of the tubular coverings are preferably made from a seamless tubing which is less susceptible of breaking, compared to prior art cover stents which use adhesive to create a seam on the covering.

Other features and advantages of the present invention will become more apparent from the following detailed description of the invention, when taken in conjunction with accompanying exemplary drawings.

BRIEF DESCRIPTION OF THE DRAWINGS

FIG. 1 is an elevational view, partially in sections, depicting a covered stent embodying features of the present invention mounted on a delivery catheter and disposed within a body vessel.

FIG. 2 is an elevational view, partially in section, similar to that shown in FIG. 1, wherein the covered stent is expanded within a vessel, compressing a lesion formed on the vessel wall.

FIG. 3 is an elevational view, partially in section, showing the expanded covered stent within the vessel after withdrawal of the delivery catheter.

FIG. 7 is a partial elevational view of an alternative embodiment in which the overlap portion of the cover material covers the stent when it is in the unexpanded configuration.

FIG. 7A is a cross-sectional view taken along line 7A—7A depicting the overlap portion of the cover material.

FIG. 8 is an enlarged partial cross-sectional view of the overlap portion of the cover material that covers the stent as depicted in FIG. 7.

FIG. 9 is a partial elevational view of the cover material with the overlap portion covering the stent in the expanded configuration.

DETAILED DESCRIPTION OF THE PREFERRED EMBODIMENTS

Figure 4:
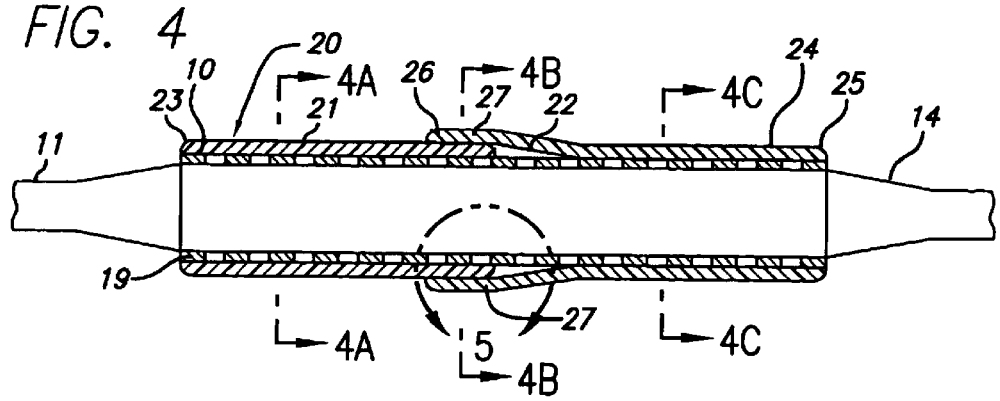
FIG. 4 is a partial elevational view of the overlap cover material and the stent assembly in the unexpanded state.

FIGS. 1–3 illustrate a first embodiment of a covered stent 10 incorporating features of the invention which is mounted onto a delivery catheter 11. The covered stent generally comprises a plurality of radially expandable cylindrical elements 12 disposed generally coaxially, interconnected by interconnecting members 13 disposed between adjacent cylindrical elements and covered with polymeric material. The delivery catheter has an expandable portion or balloon 14 for expanding the covered stent within an artery 15 or other vessel. The artery, as shown in FIG. 1, has a lesion 16 which has occluded a portion of the arterial passageway.

The delivery catheter onto which the covered stent is mounted is essentially the same as a conventional balloon dilatation catheter for angioplasty procedures. The balloon may be formed of suitable materials such as polyethylene, polyurethane, PEBAX, polyethylene terephthalate, polyvinyl chloride, nylon and ionomers such as Surlyn® manufactured by the Polymer Products Division of the Du Pont Company. Other polymers may also be used. In order for the covered stent to remain in place on the balloon during delivery to the site of the damage within the artery, the stent is compressed onto the balloon. Other means for securing the stent onto the balloon also may be used, such as providing collars or ridges on the ends of the working portion, i.e., the cylindrical portion, of the balloon. Each radially expandable cylindrical element of the covered stent may be independently expanded, therefore the balloon may be provided with an inflated shape other than cylindrical, e.g., tapered, to facilitate implantation of the covered stent in a variety of body lumen shapes.

The delivery of the covered stent can be accomplished in a number of ways. The covered stent is first mounted onto the inflatable balloon on the distal extremity of the delivery catheter. The stent may be "crimped" down onto the balloon to ensure a low profile. A heat and pressure process which increases stent security and improves the delivery profile of the composite stent/delivery catheter also could be utilized. In this particular process, the balloon is slightly inflated and heated to allow the surface of the balloon to soften, which will cause portions of the balloon material to expand between the struts of the stent. In this matter, the resulting outer surface of the inflatable balloon is formed with "ridges" which help maintain the stent on the balloon while it is being delivered through the patient's vasculature. The catheter-stent assembly then can be introduced within the patient's vasculature in a conventional Seldinger technique through a guide catheter (not shown). A guide wire 18 is disposed through the damaged arterial section having a lesion 16 and then the catheter-stent assembly is advanced over the guide wire within artery 15 until the stent is directly within the lesion. The balloon of the catheter then is expanded, expanding the covered stent against the inside of artery, which is illustrated in FIG. 2. While not shown in the drawing, the artery may preferably be expanded slightly by the expansion of the stent to seat or otherwise fix the stent to prevent movement. The lesion may also be "prediliated" by an angioplasty balloon prior to the placement of the covered stent in order to pre-expand the treatment site. In some circumstances during the treatment of stenotic portions of an artery, the artery may have to be expanded considerably in order to facilitate passage of blood or other fluid therethrough. While FIGS. 1–3 depict a vessel having a lesion, the covered stent can be used for purposes other than compressing lesions, such as supporting the vessel, reducing the likelihood of restenosis, repairing a detached lining, perforations, dissections, deliver drugs, or to assist in attaching a vascular graft (not shown) when repairing an arterial aneurysm.

The covered stent serves to hold open the artery after the catheter is withdrawn, as illustrated in FIG. 3. Due to the formation of the stent from an elongated tubular member, the cylindrical elements of the stent form a tubular opening which does not interfere with the blood flow through the artery. The covered stent will eventually be covered with endothelial cell growth which further minimizes blood flow turbulence. Furthermore, the closely spaced cylindrical elements of the stent at regular intervals provide uniform support for the wall of the artery, and consequently are well adapted to compress plaque and expand the artery as is illustrated in FIGS. 2 and 3.

Figure 5:
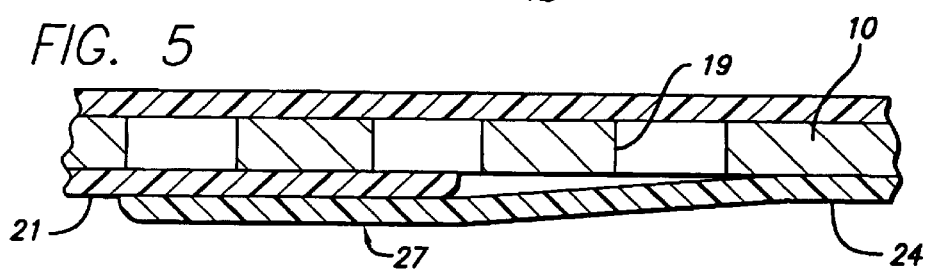
FIG. 5 is an enlarged partial cross-sectional view of the overlap portion depicted in FIG. 4.
Figure 6:
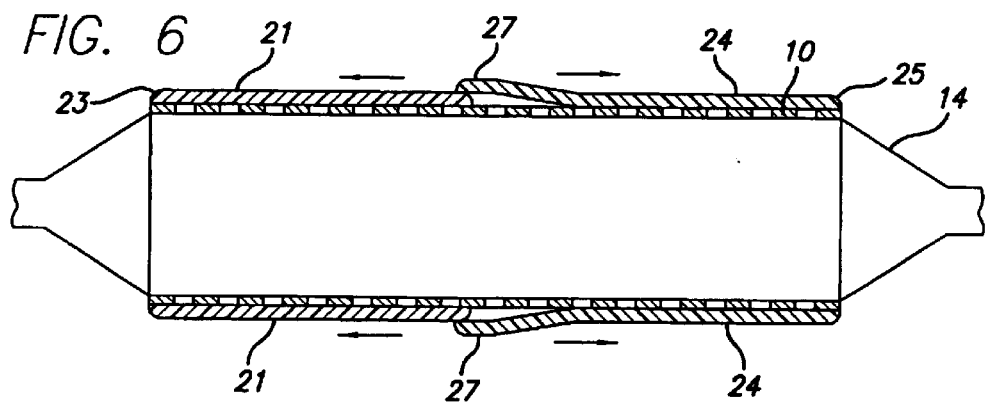
FIG. 6 is a partial elevational view of the overlap portion of the cover material and the stent assembly when the stent is in the expanded configuration.
Figure 4A:
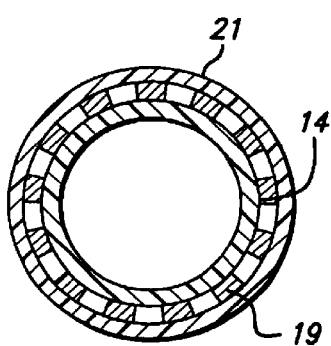
FIGS. 4A, 4B and 4C depict cross-sectional views taken along lines 4a—4a, 4b—4b, and 4c—4c, respectively, depicting the stent cover over the stent.
Figure 4B:
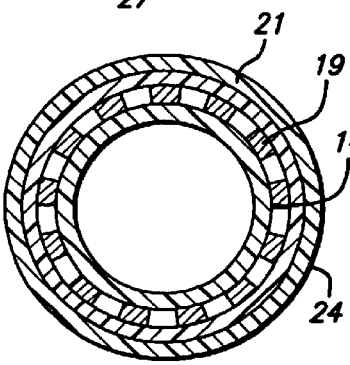
Figure 4C:
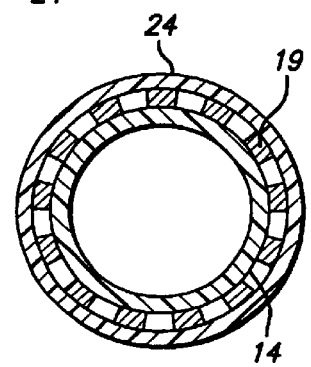

Referring now to FIGS. 4–6, the covered stent is shown with its underlying stent struts 19 and tubular cover 20. It should be appreciated that any one of the number of different stents could be utilized for the underlying stent structure 19 as the embodiments of FIGS. 1–9 are exemplary to provide examples for illustrative purposes. With respect to prior art stent designs, such as the MultiLink Stent™ manufactured by Advanced Cardiovascular Systems, Inc., Santa Clara, Calif., a plurality of cylindrical rings are connected by interconnecting members or links between adjacent cylindrical rings. Each of the cylindrical rings is formed of a repeating pattern of U-, Y-, and W-shaped members, typically having repeating patterns forming each cylindrical ring. A more detailed discussion of the configuration of the MultiLink Stent™ can be found in U.S. Pat. No. 5,569,295 (Lam) and U.S. Pat. No. 5,514,154 (Lau et al.).

It should be appreciated that the present invention can be used with stents which do not use cylindrical rings as described herein, but rather, other structural elements, such as zigzag patterns, coil patterns, and the like to create a composite stenting device.

As shown in FIGS. 4–6 the stent struts 19 are covered by tubular cover 20. In FIG. 4, the stent 10 is in the unexpanded condition as mounted on the balloon 14. The tubular cover is formed of a first section 21 having a distal end 22 and a proximal end 23 and a second section 24 also having a distal end 25 and a proximal end 26. The distal end 25 of the second section 24 is attached to the distal end of the stent by adhesive bonding, shrink bonding, or other similar methods as will be described herein. Likewise, the proximal end 23 of the first section 21 is bonded to the proximal end of the stent. In keeping with the invention, an overlap portion 27 is formed by the overlap of the first section and the second section. More specifically, the proximal end 26 of the second section overlaps the distal end 22 of the first section so that the second section is slidable relative to the first section. It is intended that the cover material 20 be substantially frictionless so that the overlapping portions can slide relative to one another. Thus, when the stent is expanded by the balloon from the configuration shown in FIG. 4, to that depicted in FIG. 6, the first section of the tubular cover slides relative to the second portion of the tubular cover at the overlap portion 27. Since the ends of the first section and the second section are attached to the stent at only one of the ends of each section, the stent and the cover will not be constrained longitudinally when expanded. Any stent shortening will be as a result of the stent material and pattern, and not due to the stent cover 20 foreshortening upon expansion. The ends of the first and second sections are shown having rounded edges which will allow the device to travel through a vessel more easily. The ends could be tapered as well. In fact, the cover material is so thin that the ends should have little or no impact on the delivery profile.

While a single overlap portion 27 is depicted in FIGS. 4–6, more than one overlap portion can be provided to suit a particular application. For example, on a particularly long stent, perhaps 30 mm or longer for coronary stents, and 50–60 mm for peripheral stents, it may be desirable to have several overlap portions in order to insure that the cover does not cause the stent to shorten upon expansion.

In another embodiment, as shown in FIGS. 7–9, a cover 30 envelopes the stent 10 and the stent struts 19. The cover has a distal end 31 and a proximal end 32 which are attached to the distal and proximal ends of the stent. An overlap portion 33 is formed in the cover material by folding a portion of the cover material onto itself so that it forms three layers, a first layer 34, a second layer 35, and a third layer 36. When the stent expands from that shown in FIG. 7 to that shown in FIG. 9, by the action of the inflated balloon, the layers of the overlap material slide relative to one another as the stent expands. Thus, the cover material does not interfere with the expansion of the stent and does not contribute to stent foreshortening, if any.

The ends of the stent cover typically are bonded to the distal and proximal ends of the stent using an adhesive, shrink bonding, melting the cover material, and the like. In order to secure the cover material to the stent, only a small portion of the cover material need be bonded to the stent. Further, there may be portions of the ends of the stent that are not covered with the cover material, depending upon the particular application. Depending, of course, on the size of the ends, the axial length of this unbonded region can be from about 60% to 90% of the total axial length of the unexpanded stent. An adhesive such as medical grade silicone can be used to bond the cover material to the stent. The adhesive could be thinned out using an organic solvent such as ethyl acetate. The covered stent could then be placed in an oven to remove excess solvent and to cure the bond. By way of example, suitable bonds have been achieved by placing covered stents in an oven for about 15 minutes at 150° Celsius. It should be appreciated, however, that the duration in the oven, along with the oven temperature, can be varied to achieve a suitable cure. The bonding agent which can be utilized to bond the ends of the covering to the stent in accordance with the present invention can be a curable adhesive or organic solvent. A primer can be used to facilitate the chemical bond between the covering and the stent. It should be appreciated that heat can be applied to the bonding agents, via an oven or other thermal source, to help in the curing and increase bond strength. These dimensions, which define the boundaries of the ends and unbonded regions of the stent and the cover, apply to all of the embodiments disclosed herein, along with any stents made in accordance with the present invention that use patterns other than cylindrical rings to create the composite stenting device.

The cover material used with the present invention can be made from any number of materials, including polyurethane, polyethyleneterephthalate (PET), or ePTFE.

When polyurethane is used to form the cover 20 it should be made with tubing which has no seams to help prevent the possibility of the cover tearing during usage. In some prior art devices, the outer covering is made from a single sheet of material which is wrapped around the stent and glued to create a seam that extends along the length of the stent axis. The use of a tubular member to form the cover avoids the possibility that the glue seam could rip or tear during expansion. The advantage of using a tubular segment of polyurethane is the ease of attaching the ends of the covering to the underlying stent 20 which results in a composite device which is strong yet flexible and fully expandable. Another advantage of using polyurethane is that the material can be relatively easily impregnated with drugs, which would be released through the polyurethane into the body vessel once the covered stent is placed in the vessel. Additionally, surface modified polyurethanes, such as Biospan S (The Polymer Technology Group, Berkeley, Calif.) or ThoraLon (Thoratec, Pleasanton, Calif.), could also be utilized as the material to form the cover 20.

The cover 20 could be made from materials such as polyethylene terephtholate (PET) or ePTFE which can be obtained in a tubular form to fit over the stent 10. One advantage of using a ePTFE material is that the material can be extruded in a tubing having a specific porosity. The porosity can range from about 5 to 200 microns which should permit cellular migration through the covering. Another advantage of using ePTFE tubing is that it can easily impregnated with drugs, which would be released into the body vessel and could improve the performance of the covered stent once its implanted. A covering made from ePTFE tubing could be applied to the unexpanded stent 10 in the same manner described above with the ends of the cover 20 being bonded to the ends of the stent.

The thicknesses of the various coverings utilized in conjunction with the present invention can vary from 0.0005 to 0.010 inch (about 12 microns to about 250 microns). In one embodiment, the covered material is ePTFE tubing having an inside diameter of 0.056+/−0.0004 inch and a wall thickness of 0.002+/−0.0010 inch. The porosity of the coverings can also be varied depending upon the particular use for the covered stent. Also, openings formed in the covering could be formed, along with the particular pattern depending upon the particular application for the covered stent.

All of the coverings used in accordance with the present invention can be provided with openings which are formed, for example, by a laser. The material forming the covering also could be formed having a certain degree of porosity. The openings and porous nature of the material allow some cell infiltration through the covering to speed up the process of endothelialization. Such a covering would also allow nutrient transfer to the walls of the vessel from the resulting blood flow. Both of these occurrences would more likely result in better acceptance of the covering by the blood vessel, reducing the chance that the body will reject the implant. The material also can be nonporous, depending upon the particular application to which the covered stent is to be used. Additionally, all of the tubular coverings are preferably made from a seamless tubing which is less susceptible of breaking, compared to prior art covered stents which use adhesive to create a seam on the covering. The coverings also can be loaded with drugs which will be released in the area of treatment to improve the device's performance within the body vessel.

While the invention has been illustrated describing terms of use as intravasculature stents, it will be apparent to those skilled in the art that the covered stents of the present invention can be used in other instances in all vessels of the body. Since the covered stents of the present invention have the features of being expandable to large diameters while retaining their structural integrity and with minimal shortening, they are particularly well suited for implantation in almost any vessel in which such devices can be used. Other modifications and improvements may be made without departing from the scope of the present invention.

What is claimed:

1. A stent assembly, comprising:
   an intravascular stent;
   a cover material surrounding the stent and having a first section and a second section, the first and second sections forming an overlap portion;
   the overlap portion being configured so that the first section and the second section are slidable with respect to each other along the longitudinal axis of the stent;
   wherein the cover material has a distal end and a proximal end;
   and the cover material distal end and proximal end are attached to the stent;
   wherein the overlap portion is positioned between the distal end and the proximal end of the cover material; and
   wherein the first section has a proximal end and a distal end and the first section is shorter than the overall length of the stent.

2. The assembly of claim 1, wherein the second section has a proximal end and a distal end and the second section is shorter than the overall length of the stent.

3. The assembly of claim 2, wherein the proximal end of the second section forms the overlap portion with the distal end of the first section.

4. The assembly of claim 1, wherein the stent has a distal end and a proximal end and wherein the cover material is attached to the stent at the stent distal end and the stent proximal end.

5. The assembly of claim 1, wherein the cover material is formed of more than two sections.

6. The assembly of claim 5, wherein the more than two sections of the cover material form more than one overlap portion along the stent.

7. The assembly of claim 1, wherein the cover material has a thickness in the range of 0.0005 to 0.010 inch.

8. The assembly of claim 1, wherein the cover material can be formed of either porous or non-porous material.

9. A covered stent assembly, comprising:
   an intravascular stent having a distal end and a proximal end;
   a tubular cover material covering at least a portion of the stent wherein the cover material is formed of a first section and a second section; and
   the first section and second section each having a proximal end and a distal end, wherein the proximal end of the second section and the distal end of the first section are slidable along the longitudinal axis of the stent and form an overlap portion so that as the stent expands the overlap portion shortens along the longitudinal axis of the stent.

10. The assembly of claim 9, wherein the cover material has a distal end and a proximal end.

11. The assembly of claim 10, wherein the cover material distal end and proximal end are attached to the stent.

12. The assembly of claim 11, wherein the overlap portion is positioned between the distal end and the proximal end of the cover material.

13. The assembly of claim 10, wherein the cover material is attached to the stent at the stent distal end and the stent proximal end.

14. The assembly of claim 13, wherein the cover material is attached to the stent by an adhesive.

15. The assembly of claim 9, wherein the first section is shorter than the overall length of the stent.

16. The assembly of claim 9, wherein the second section is shorter than the overall length of the stent.

17. The assembly of claim 16, wherein the first section and the second section are configured for relative sliding movement at the overlap portion when the stent is expanded.

18. The assembly of claim 9, wherein the cover material is formed from a biocompatible material taken from the group of materials consisting of ePTFE, PET and polyurethane.

19. The assembly of claim 9, wherein the cover material is formed of more than two sections.

20. The assembly of claim 19, wherein the more than two sections of the cover material form more than one overlap portion along the stent.

21. The assembly of claim 9, wherein the cover material has a thickness in the range of 0.0005 to 0.010 inch.

22. The assembly of claim 9, wherein the cover material can be formed of either porous or non-porous material.

* * * * *